United States Patent
Fadler et al.

(10) Patent No.: US 7,901,135 B2
(45) Date of Patent: Mar. 8, 2011

(54) DISPLACEMENT SYSTEM FOR AN X-RAY C-ARM

(75) Inventors: Franz Fadler, Hetzles (DE); Norbert Herrmann, Ebnath (DE); Manfred Sechser, Neusorg (DE)

(73) Assignee: Siemens Aktiengesellschaft, München (DE)

( * ) Notice: Subject to any disclaimer, the term of this patent is extended or adjusted under 35 U.S.C. 154(b) by 54 days.

(21) Appl. No.: 12/490,950

(22) Filed: Jun. 24, 2009

(65) Prior Publication Data

US 2010/0027760 A1 Feb. 4, 2010

(30) Foreign Application Priority Data

Jun. 30, 2008 (DE) .................. 10 2008 030 828

(51) Int. Cl.
*H05G 1/02* (2006.01)
(52) U.S. Cl. .................................... 378/196; 378/197
(58) Field of Classification Search .......... 378/193–198
See application file for complete search history.

(56) References Cited

U.S. PATENT DOCUMENTS 6,609,826 B1 * 8/2003 Fujii et al. .................. 378/198

FOREIGN PATENT DOCUMENTS

DE 197 29 657 A1 1/1999
DE 10 2005 035 248 A1 2/2007

OTHER PUBLICATIONS

German Office Action dated Feb. 10, 2009 with English translation.

* cited by examiner

*Primary Examiner* — Courtney Thomas
(74) *Attorney, Agent, or Firm* — Brinks Hofer Gilson & Lione

(57) ABSTRACT

A displacement system for a C-arm arranged on a trolley is provided. The displacement system includes at least a first and at least a second guiding element arranged in a plane or parallel thereto. The first and second guiding element are arranged at right angles to one another and a displacement device arranged in a displaceable fashion along the first and second guiding element, with the displacement device being coupled to the guiding elements such that by rotating the displacement device about a drive axis, the displacement device is moved along the first and second guiding element. As a result, the displacement system prevents jamming as a result of leverage forces during displacement of the C-arm.

12 Claims, 3 Drawing Sheets

DISPLACEMENT SYSTEM FOR AN X-RAY C-ARM

This patent document claims the benefit of DE 10 2008 030 828.5 filed Jun. 30, 2008, which is hereby incorporated by reference.

BACKGROUND

Mobile x-ray devices with C-arms are used in surgical interventions in operating rooms (theaters). The extensive mobility of the C-arm x-ray systems makes them straightforward for the medical staff to move away from and back to the patient on the operating table while an operation is in progress. For the sake of rationalization and during use in small operating rooms, it is advantageous not to have to move the relatively heavy C-arm x-ray systems in their entirety too often. It is preferable to move the C-arm, rather than the entire C-arm system. The C-arm includes an x-ray emitter and x-ray detector. The positions, which have already been assumed, can be reassumed automatically and precisely.

U.S. Pat. No. 6,609,826 B1 describes the way in which a C-arm can be moved horizontally to and in parallel with a patient support (bed). U.S. Pat. No. 6,609,826 B1 discloses a moving apparatus between a C-arm and a retaining device, with the C-arm being moveable in a horizontal direction at right angles to one arm. However, the parallel linear guides used and the weight of the C-arm can cause the moving apparatus to jam as a consequence of the unfavorable leverage ratio between the displacement force applied and the distance to the linear guides.

DE 10 2005 035 248 A1 describes a displacement apparatus for adjusting the ventilation canals using an actuation facility in a car. The apparatus for ventilating vehicles includes at least one nozzle. The outflow direction of the nozzle can be adjusted and an actuation facility arranged at least partially outside the nozzle in order to adjust the outflow direction of the nozzle. The actuation facility has a first actuation element, which can be rotated about a first geometric axis and a second actuation element which can be moved in respect of a second geometric axis in order to adjust the outflow direction. A control facility for controlling both actuation elements is also provided. The control facility may be connected to the actuation elements such that the first actuation and the second actuation element are moved by a control of the control device in a first control direction and a control of the control device in a second control direction in each instance.

DE 197 29 657 A1 discloses a robotic arm with two guiding shafts and a spindle, which are at right angles to one another. The guiding shafts and the spindle are connected by half rods of the telescopic arm and allow a vertical linear movement of a connecting piece.

SUMMARY AND DESCRIPTION

The present embodiments may overcome one or more of the drawbacks or limitations inherent in the related art. For example, in one embodiment, a displacement (i.e., movement) system may provide a movement of an x-ray C-arm which is parallel to a patient support.

In one embodiment, a displacement system for a C-arm arranged on a trolley is provided. The displacement system includes at least one first and at least one second guiding element arranged in a plane or parallel to the plane. The first and second guiding elements may be arranged at right angles to one another and a displacement device may be arranged in displaceable (moveable) fashion along the first and second guiding elements, with the displacement device being coupled to the guiding elements such that the displacement device is moved along the first and second guiding element by rotating the displacement device about a drive axis.

The displacement system may include a first rotary disk which is connected to the displacement device in a manner so as to be rotatable about a axis of rotation which is parallel to the drive axis, a second rotary disk which is connected to the displacement device so as to be rotatable about the drive axis and a belt connecting the first and second rotary disk, with the displacement device being rotated about the drive axis when the second rotary disk is rotated about the drive axis, by the first rotary disk being moved along the first guide element by the belt. This is advantageous in that a jamming of the displacement apparatus due to leverage forces is prevented.

The plane can be horizontally aligned. As a result, the displacement device can be moved, for example, in parallel with a base surface and a patient support.

In one embodiment, the drive axis can be arranged at right angles to the plane. Arranging the drive axis at right angles to the plane is advantageous for a stable and secure force transmission to take place on the displacement device.

The belt may be a toothed belt. The toothed belt is advantageous in terms of reliable force transmission.

A leverage force acting on the displacement device may be partially introduced into the second guiding element. This results in the leverage force being divided onto components which are at right angles to one another.

In a further embodiment, the displacement device may include a guiding pin which can be moved in the first guiding element and a carriage which can be moved in or on the second guiding element. The simple and friction-free guidance is advantageous.

The first guiding element may include a first rail system and the second guiding element may include a second rail system. As a result, friction-free guidance is ensured.

The displacement device may be moved approximately +/−200 mm about a central position along the first guiding element. This offers adequate room to maneuver for a displacement along a patient support.

A C-arm may include a displacement apparatus. The C-arm may be arranged on the displacement device such that it can be moved in parallel to a patient couch. As a result, the C-arm may be easily and automatically used in the operating room in a repositionable fashion.

In one embodiment, an x-ray apparatus may include the C-arm having the displacement apparatus.

DETAILED DESCRIPTION

Figure 1:
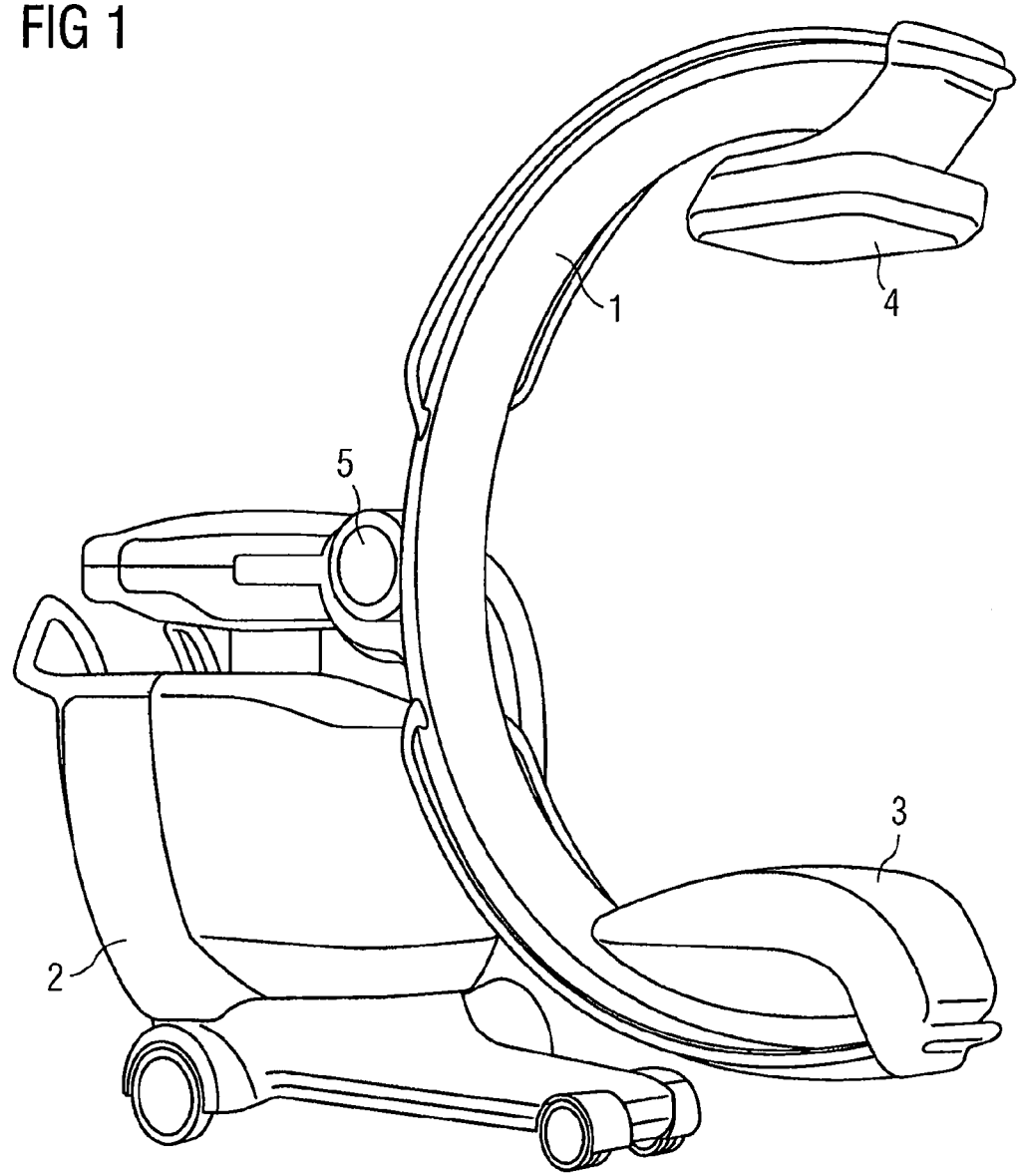
FIG. 1 shows one embodiment of a mobile C-arm x-ray device.

FIG. 1 shows a perspective view of a mobile C-arm x-ray system, which may be referred to as a displacement (movement) system. The mobile C-arm x-ray system includes an x-ray C-arm 1. The x-ray C-arm 1 is arranged on a trolley 2 with rollers. The x-ray C-arm 1 and the trolley 2 are connected to one another by a C-arm retaining module 5. An x-ray emitter 3 and/or x-ray detector 4 are positioned at the ends of the x-ray C-arm 1. A patient located on a patient support can be irradiated with x-rays, for example, with an x-ray emitter 3. The x-rays may be absorbed by the x-ray detector 4. The x-ray C-arm 1 connected to the C-arm retaining module 5 may be moved horizontally by a displacement apparatus.

Figure 2:
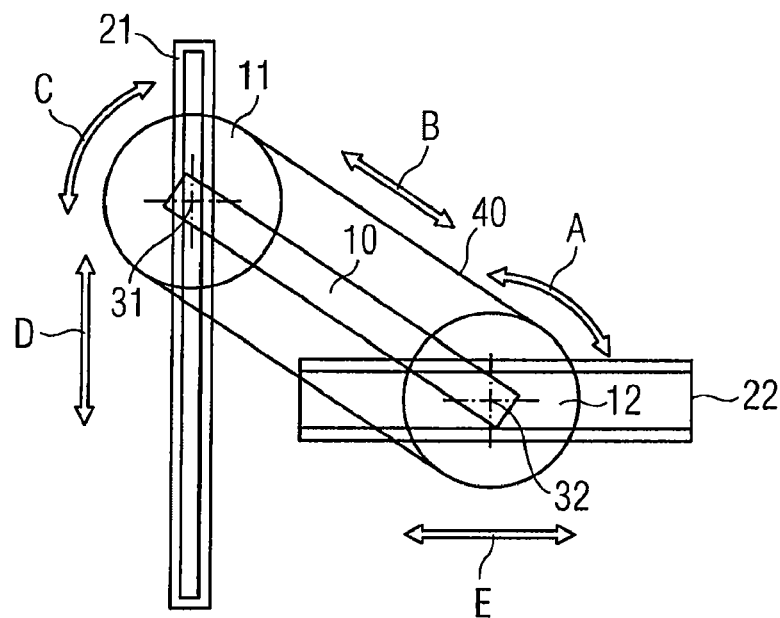
FIG. 2 shows one embodiment of a displacement apparatus having a double swivel.

FIG. 2 shows a displacement device having a double swivel. A first guiding element 21 and a second guiding element 22 are arranged in parallel in a plane or in parallel with the plane. The two guiding elements 21, 22 may be at right angles to one another. A displacement device 10 is arranged in a displaceable fashion in parallel with the first guiding element 21 and the second guiding element 22. The displacement device may be displaceably coupled to both guiding elements 21, 22. In order to couple with the guiding elements 21, 22, the displacement device 10 includes a second rotary disk 12, also known as a second swivel, which is connected to the displacement device 10 so as to be rotatable about a drive axis 32. The second axis of rotation 12 includes a first rotary disk 11 arranged at the other end of the displacement device 10 is actively connected to a belt 40, for example, a toothed belt. The first rotary disk 11, also known as a first swivel, is rotatably connected to the displacement device 10. The displacement element 10 is rotatable about the first axis of rotation 31. The first guiding element 21 has a groove, in which a guiding pin is guided below the first swivel 11. The displacement element 10 is rotated about the second rotary disk 12 by a drive device, shown by the direction of rotation A. As a result of the first rotary disk 11 rotating about the axis of rotation 31, the displacement device 10 moves along the first guiding element 21 in direction D. The guiding pin allows the displacement device 10 to be held in the groove of the first guiding element 21 and cannot deviate in another direction. The displacement device 10 may perform a longitudinal balance E along the second guiding element 22 as a balance in respect of the movement of the displacement device 10 along the first guiding element 21.

Figure 3:
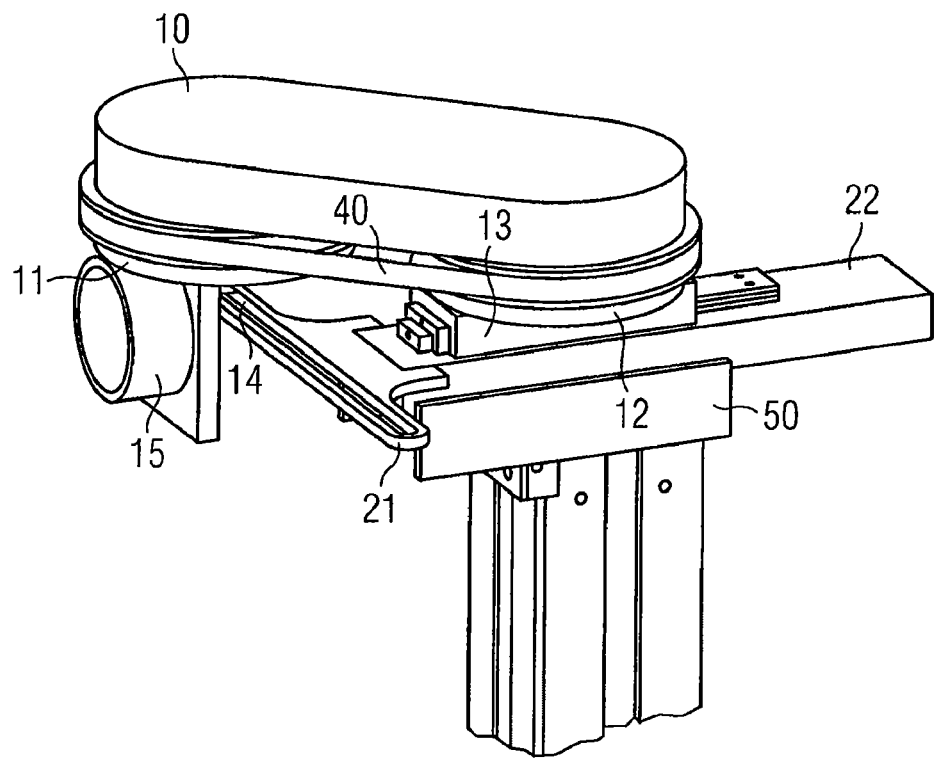
FIG. 3 shows a perspective view of one embodiment of a displacement apparatus having a double swivel.
Figure 4:
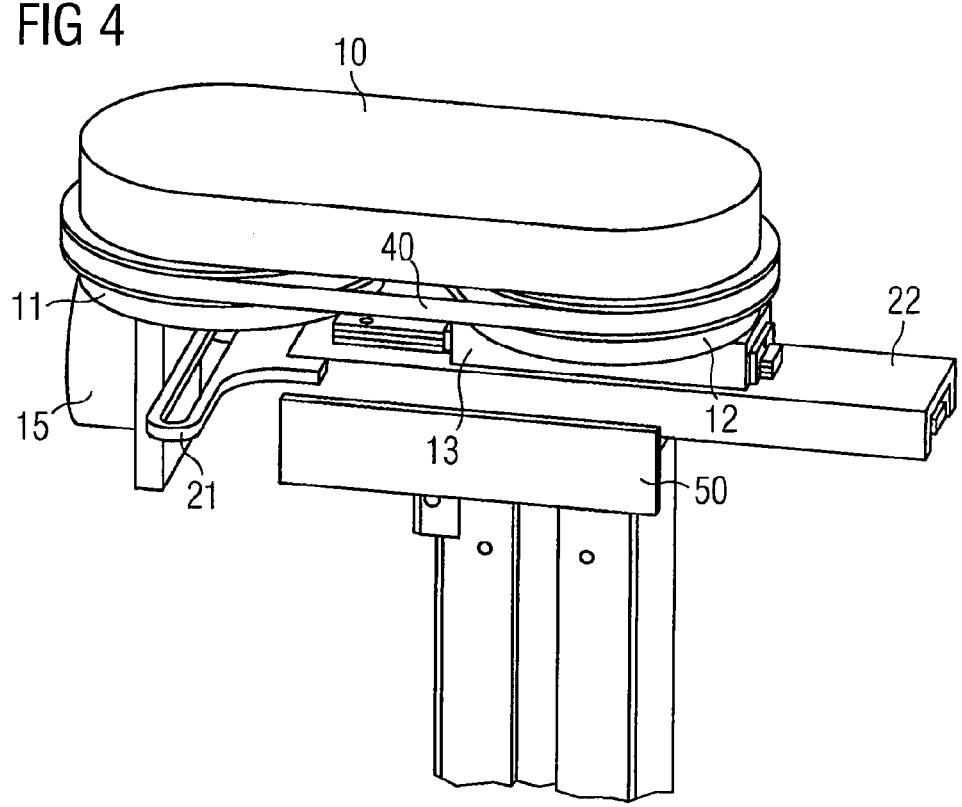
FIG. 4 shows a further perspective view of the displacement apparatus having a double swivel.
Figure 5:
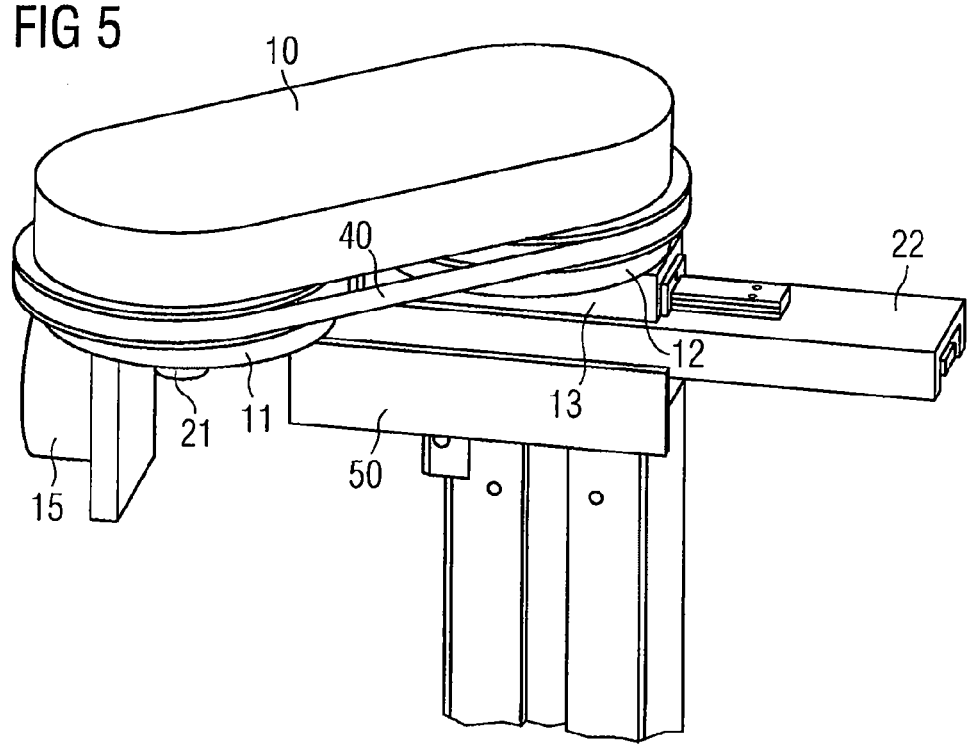
FIG. 5 shows a further perspective view of the displacement apparatus having a double swivel.

FIGS. 3, 4 and 5 show perspective views of a displacement system in different displacement positions. A first guiding element 21 and a second guiding element 22 at right angles thereto are fixedly arranged on a carrier plate 50. The two guiding elements 21, 22 are positioned in a plane or are arranged in parallel to the plane. The two guiding elements 21, 22 may be embodied as a rail system. A first rail system 21 is shown, which has a groove, in which a guiding pin 14 connected to a displacement device 10 can be guided in a moveable fashion. The guiding pin 14 is part of the displacement device 10, which is coupled in a moveable fashion to both guiding elements 21, 22. This coupling takes place by a first rotary disk 11, also known as a first swivel, which is arranged above the first guiding element 21, which is rotatably connected to the displacement device 10. The displacement device 10 is provided with a second rotary disk 12 on its other end, said rotary disk 12 being arranged above the second guiding element 22. The second rotary disk 12 can be moved when the first rotary disk 11 is rotated using a toothed belt 40 such that the displacement device 10 moves along the first guiding element 21 and along the second guiding element 22. The first guiding element 21 forces the displacement device 10 to move along the first guiding element 21. As a result, the displacement device 10 has to move out along the second guiding element 22 by a longitudinal movement.

A coupling element 15 may be fixedly connected to the first rotary disk 11. The C-arm may be mounted on the coupling element 15. A carriage 13, which is rotatable with respect of the second rotary disk 12, is arranged below the second rotary disk 12. The carriage 13 can slide to and fro on the second guiding element 22 and thus performs the compensating motion.

FIG. 3 shows the displacement device 10 in a position moved to a central position. In this position the coupling element 15 has a maximum horizontal displacement.

FIG. 4 shows the displacement device 10 in a central position. The carriage 13 of the displacement device 10 reaches a final position on the second guiding element 22. The coupling element 15 is not moved.

FIG. 5 shows the displacement device 10 in a position which mirror images FIG. 3. In this position, the coupling element 15 has a horizontal displacement which is maximum in respect of the central position.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A displacement system for a C-arm arranged on a trolley, the displacement system comprising:
    at least one first and at least one second guiding element arranged in a plane or parallel to said plane, with the first and second guiding elements being arranged at right angles to one another,
    a displacement device arranged in a displaceable fashion along the first and second guiding elements, with the displacement device being coupled to the guiding elements such that by rotating the displacement device about a drive axis, the displacement device is displaced along the first and second guiding elements,
    a first rotary disk connected in a rotatable fashion to the displacement device about an axis of rotation which is parallel to the drive axis,
    a second rotary disk connected in a rotatable fashion to the displacement device about the drive axis, and
    a belt connecting the first and second rotary disks, with the displacement device being rotated about the drive axis when the second rotary disk is rotated about the drive axis, by the first rotary disk being moved along the first guiding element by the belt.

2. The displacement system as claimed in claim 1, wherein the plane is aligned horizontally.

3. The displacement system as claimed in claim 1 or 2, wherein the drive axis is arranged at right angles to the plane.

4. The displacement system as claimed in claim 1, wherein the belt is a toothed belt.

5. The displacement system as claimed in claim 1, wherein a leverage force acting on the displacement device is operable to be partially introduced into the second guiding element.

6. The displacement system as claimed in claim 1, wherein the first rotary disk includes a guiding pin that is operable to be moved in the first guiding element.

7. The displacement system as claimed in claim 1, further comprising a carriage that is operable to travel in or on the second guiding element and is arranged below the second rotary disk.

8. The displacement system as claimed in claim 1, wherein the first guiding element includes a first rail system and the second guiding element includes a second rail system.

9. The displacement system as claimed in claim 1, wherein the displacement device is operable to be moved approximately +/−200 mm about a central position along the first guiding element.

10. The displacement system as claimed in claim 1, further comprising a coupling element that is fixedly connected to the first rotary disk such that the coupling element is operable to be moved in parallel with the first guiding element.

11. A C-arm comprising:
an x-ray emitter operable to emit x-rays;
an x-ray detector operable to detect x-rays emitted from the x-ray emitter; and
a displacement system comprising:
at least one first and at least one second guiding element arranged in a plane or parallel to said plane, with the first and second guiding elements being arranged at right angles to one another,
a displacement device arranged in a displaceable fashion along the first and second guiding elements, with the displacement device being coupled to the guiding elements such that by rotating the displacement device about a drive axis, the displacement device is displaced along the first and second guiding elements,
a first rotary disk connected in a rotatable fashion to the displacement device about an axis of rotation which is parallel to the drive axis,
a second rotary disk connected in a rotatable fashion to the displacement device about the drive axis, and
a belt connecting the first and second rotary disks, with the displacement device being rotated about the drive axis when the second rotary disk is rotated about the drive axis, by the first rotary disk being moved along the first guiding element by the belt,
wherein the C-arm is arranged on the coupling element such that the C-arm is operable to be moved in parallel with a patient support.

12. An x-ray system comprising:
a C-arm comprising:
an x-ray emitter operable to emit x-rays;
an x-ray detector operable to detect x-rays emitted from the x-ray emitter; and
a displacement system comprising:
at least one first and at least one second guiding element arranged in a plane or parallel to said plane, with the first and second guiding elements being arranged at right angles to one another,
a displacement device arranged in a displaceable fashion along the first and second guiding elements, with the displacement device being coupled to the guiding elements such that by rotating the displacement device about a drive axis, the displacement device is displaced along the first and second guiding elements,
a first rotary disk connected in a rotatable fashion to the displacement device about an axis of rotation which is parallel to the drive axis,
a second rotary disk connected in a rotatable fashion to the displacement device about the drive axis, and
a belt connecting the first and second rotary disks, with the displacement device being rotated about the drive axis when the second rotary disk is rotated about the drive axis, by the first rotary disk being moved along the first guiding element by the belt,
wherein the C-arm is arranged on the coupling element such that the C-arm is operable to be moved in parallel with a patient support.

\* \* \* \* \*